United States Patent [19]

Lauritzen

[11] Patent Number: 4,549,653
[45] Date of Patent: Oct. 29, 1985

[54] ADHESIVE BANDAGE AND PACKAGE

[75] Inventor: Nels J. Lauritzen, Piscataway, N.J.

[73] Assignee: Johnson & Johnson Products, Inc., New Brunswick, N.J.

[21] Appl. No.: 529,463

[22] Filed: Sep. 6, 1983

[51] Int. Cl.[4] .............................................. B65D 73/00
[52] U.S. Cl. ................... 206/441; 206/440; 206/447; 206/820
[58] Field of Search ............. 206/438, 440, 441, 447, 206/460, 820; 229/69

[56] References Cited

U.S. PATENT DOCUMENTS

| | | | |
|---|---|---|---|
| 2,142,194 | 1/1939 | Karfiol | 206/820 |
| 2,205,437 | 6/1940 | Ringler | 206/602 |
| 2,292,995 | 8/1942 | Greenwoll | 206/820 |
| 2,353,332 | 7/1944 | Hall | 206/440 |
| 2,522,963 | 9/1950 | Rogers | 206/441 |
| 2,703,083 | 3/1955 | Gross | 128/156 |
| 2,752,038 | 6/1956 | Abbott | 206/441 |
| 2,897,961 | 8/1959 | Bush | 206/441 |
| 2,924,331 | 2/1960 | Hoey | 206/441 |
| 2,927,689 | 8/1960 | Look, Jr. | 206/441 |
| 2,946,435 | 7/1960 | Schladermundt et al. | 206/441 |
| 2,965,223 | 12/1960 | Schladermundt et al. | 206/441 |
| 2,969,144 | 1/1961 | Zackheim | 206/441 |
| 2,969,145 | 1/1961 | Hannauer, Jr. | 206/441 |
| 2,973,859 | 3/1961 | Schladermundt et al. | 206/441 |
| 3,007,571 | 11/1961 | Marinaro | 206/441 |
| 3,018,881 | 1/1962 | Wall | 206/441 |
| 3,062,371 | 11/1962 | Patience | 206/440 |
| 3,072,249 | 1/1963 | Tritsch | 206/441 |
| 3,313,405 | 4/1967 | Blackford | 206/441 |
| 3,443,686 | 5/1969 | Raymond | 206/460 |
| 3,530,494 | 9/1970 | Baratta | 206/441 |
| 3,622,265 | 10/1971 | Dickerson | 55/56 |
| 3,790,070 | 2/1974 | Schnitzer et al. | 229/69 |
| 3,854,654 | 12/1974 | Van Malderghem | 229/69 |
| 4,182,448 | 1/1980 | Huck et al. | 206/460 |
| 4,182,449 | 1/1980 | Kozlow | 206/441 |
| 4,264,008 | 4/1981 | Kozlow | 206/441 |
| 4,436,205 | 3/1984 | Horii | 206/530 |

FOREIGN PATENT DOCUMENTS 498410 1/1951 Belgium .............................. 206/440

Primary Examiner—William T. Dixson, Jr.
Assistant Examiner—Brenda J. Ehrhardt
Attorney, Agent, or Firm—Wayne R. Eberhardt

[57] ABSTRACT

A packaged adhesive bandage comprising a bandage backing strip having an adhesive coating and a wound covering pad on one surface thereof contained in a sealed envelope with the side edges of the backing strip laminated and sealed between the panels of the envelope. The packaged bandage is produced by a continuous process wherein a length of wrapper material is folded to enclose a length of bandage material and individual bandages are cut transversely from the folded material with simultaneous sealing of the cut edges.

12 Claims, 10 Drawing Figures

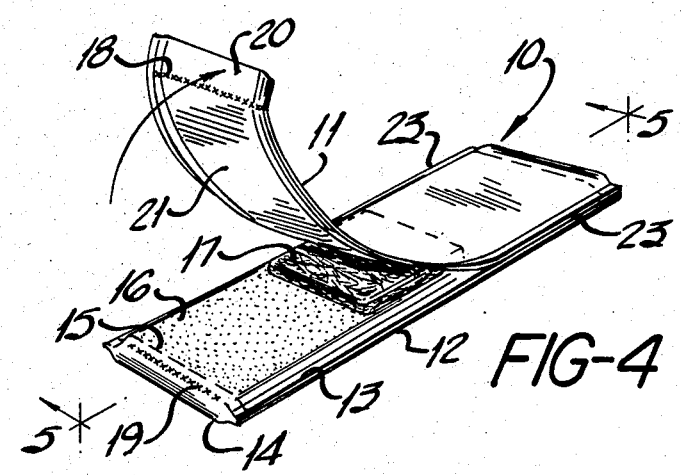
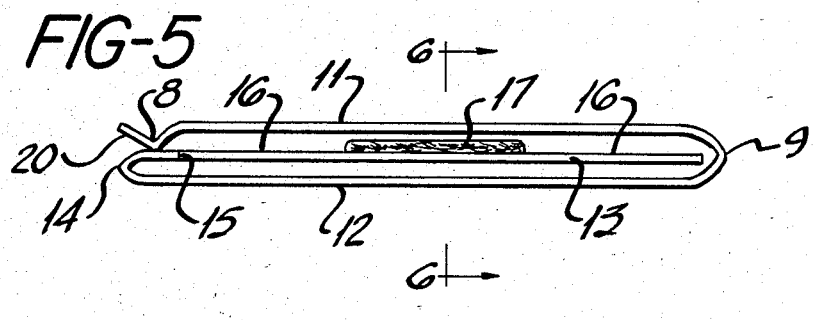
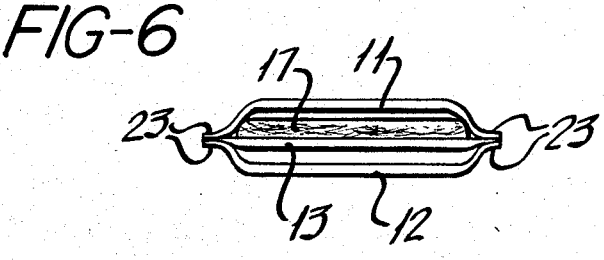

ADHESIVE BANDAGE AND PACKAGE

FIELD OF INVENTION

The present invention relates to individually packaged adhesive bandages and more particularly to a bandage and envelope combination which provides for ease of manufacture and an improved bandage delivery system.

BACKGROUND OF THE INVENTION

Adhesive bandages comprising a central pad area and adjacent adhesive areas are well known in the art and popular as first aid wound dressings. Current bandages generally comprise an elongated strip of cloth or plastic backing material coated on one surface with a pressure sensitive adhesive. A gauze or sponge pad is secured to the adhesive surface in a central location to serve as the wound covering material. The wound facing surface of the pad may be plastic coated or otherwise treated to prevent the pad from adhering to the wound. Plastic coated release strips are placed over the adhesive areas and the entire assembly is enclosed in a sealed package and sterilized to be ready for use.

The adhesive bandages of the prior art are characterized by their construction of two separate components, i.e., the bandage proper and the enveloping package. The application of the adhesive surface release strips and the packaging of individual bandages requires additional handling and materials which increases the manufacturing costs. It is accordingly an object of the present invention to provide an improved adhesive bandage. It is a further object of this invention to provide a low cost adhesive bandage through the use of inexpensive materials and low cost manufacturing techniques, and through the elimination of the adhesive surface release strips.

A yet further object of the present invention is to provide a method for producing an adhesive bandage and a wrapper or envelope therefor on a continuous basis from a source of composite bandage and wrapper material. A still further object of this invention is to provide a packaged adhesive bandage having an improved bandage delivery system wherein the bandage is presented for application to the wound immediately as the package is opened. These and other objects of the present invention will be apparent from the ensuing description and claims.

SUMMARY OF THE INVENTION

A packaged adhesive bandage comprising a bandage having a wound covering pad secured to a tacky adhesive coating on one surface of the backing strip thereof and contained in a protective wrapper or envelope sealed around the periphery to enclose the bandage between two panels. The backing strip of the bandage is sealed between the panels of the envelope along the side edges and thus becomes an integral part of the package. One end of the bandage is temporarily attached to or retained by the base panel of the package which faces the adhesive free side of the bandage. The opposing panel of the package which faces the adhesive coated side of the bandage is provided with an adhesive release coating and forms a removable cover panel of the package. Pull tabs are provided on one end of the envelope proximate to the attached end of the bandage to facilitate removal of the cover panel.

Upon removal of the cover panel, the bandage remains secured to the base panel proximate to the pull tabs and further remains sealed to that panel along the side edges with the adhesive coated surface of the bandage now exposed. The bandage is conveniently positioned on the wound and, with the adhesive holding the bandage in place, the base panel of the package is readily separated from the bandage.

Economic advantages are obtained in the manufacure of the bandage since bandage and wrapper materials may be assembled in a continuous length and then folded, sealed and cut in a continuous process to form individual wrapped bandages. The bandage material may be an extension of the package material detachably secured thereto by a line of perforations or other line of weakness to permit deliberate separation of the bandage from the envelope at the time of application.

Alternatively, the bandage material may be different than the envelope material and detachably secured thereto by heat sealing, adhesive attachment or by other means whereby the security of attachment is sufficient to permit bandage manufacture while still permitting deliberate separation of the bandage from the wrapper at the time of use. In one embodiment, the end of the bandage backing material is gripped in a fold at the end of the base panel and restrained by the edge seal of the envelope until the base panel is unfolded upon application of the bandage.

In a preferred method for the manufacture of the packaged bandage of the present invention, the bandage material and the wrapper material are joined side-by-side and form a continuous length of composite sheet material. A coating of a suitable pressure sensitive adhesive is applied to the bandage material and a wound covering pad is positioned on the adhesive surface if desired. Individual pads of fabric, foam or other suitable pad material may be positioned on the backing strip with spacing corresponding to the final width of the bandage. Alternatively a continuous strip of pad material may be laid onto the backing strip provided the composition of the pad material is selected to not interfere with final sealing along the side edges of the package. In a further embodiment, the wound covering fabric is omitted from the bandage and the backing strip forms a wound covering film which may include an adhesive coating or be adhesive free over the wound covering area.

The material of the wrapper or envelope is provided with an adhesive release surface over at least the cover panel which faces the adhesive coated surface of the bandage in the final package. This adhesive release surface may be provided as a coated surface on the wrapper stock material or a release coating or film may be applied to the wrapper material as part of the bandage manufacturing process.

The composite bandage and wrapper material is folded twice to enclose the bandage within the wrapper, and the open end of the wrapper heat is sealed to the underlying material to secure the fold while providing pull tabs for subsequent opening of the package. Individual bandages are then die cut with edge sealing along lines spaced according to the desired width of the final bandage product.

In an alternative method of manufacture, a continuous length of the adhesive coated bandage material is positioned between continuous lengths of wrapper cover material and wrapper base material. The wrapper materials are sealed along the edges to enclose the bandage therebetween in such a manner that pull tabs are provided along one edge of the wrapper material. The resulting composite laminate may then be die cut transversely with edge sealing as previously described to obtain individually packaged bandages with the bandage material detachably secured to the wrapper base material at the end proximate to the pull tabs.

DESCRIPTION OF THE DRAWINGS

FIG. 4 is a view in perspective of an individual bandage prepared from the material of FIG. 1 with the cover panel of the package partially removed.

FIG. 5 is an expanded schematic side view of the package of FIG. 4 through line 5—5.

FIG. 6 is an expanded end view in cross section of the package of FIG. 5 through line 6—6.

DETAILED DESCRIPTION OF THE INVENTION

Figure 1:
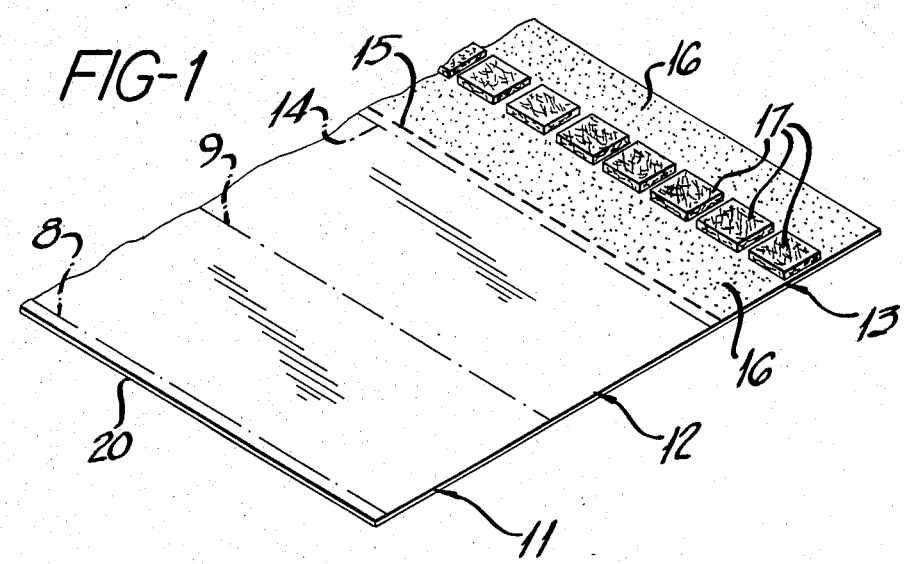
FIG. 1 is a view in perspective of a continuous length of composite bandage and wrapper material.
Figure 2:
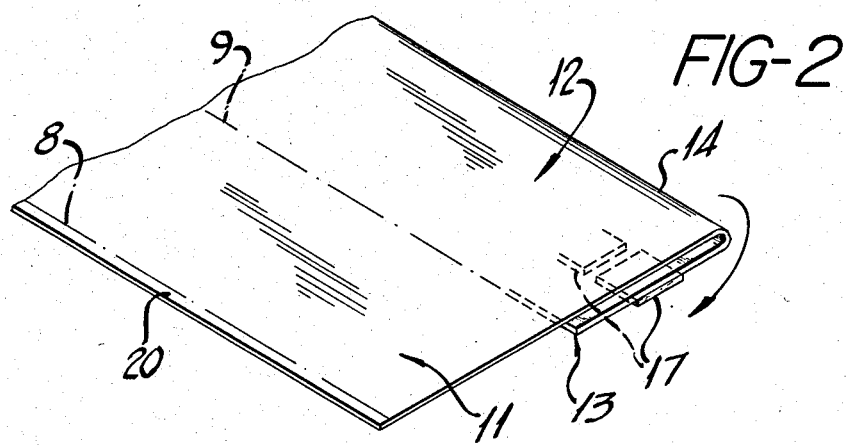
FIG. 2 is a view in perspective of the material of FIG. 1 with the initial fold to enclose the bandage material.
Figure 3:
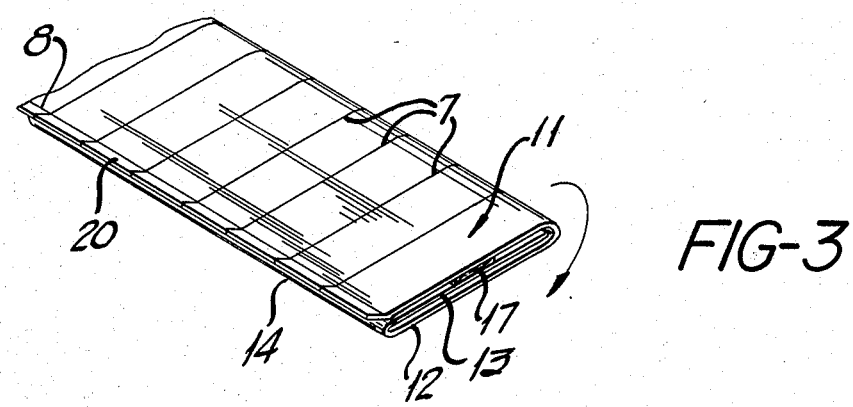
FIG. 3 is a view in perspective of the material of FIG. 1 and FIG. 2 with the final fold to enclose the bandage material.

With reference to FIGS. 1-3 inclusive, there is illustrated a continuous length of composite bandage and wrapper material, and the method of folding such material to totally enclose the bandage prior to cuttihg individual bandages from the continuous length of folded composite material.

Turning first to FIG. 1, there is illustrated a continuous length of composite material comprising bandage material 13 and a wrapper material comprising base portion 12 and cover portion 11. Bandage material 13 is coated on one side with adhesive 16 and includes wound covering pads 17 adhesively secured thereto and spaced according to the intended final width of the individual bandage. The bandage material and the wrapper material are formed from a single width of plastic film or other suitable material which has been perforated along line 15 to provide a line of weakness whereby the bandage portion may be readily separated from the wrapper portion at the time of use.

The composite sheet of material of FIG. 1 is folded to enclose the bandage within the confines of the wrapper as further illustrated in FIGS. 2 and 3. The first fold illustrated in FIG. 2 is taken along line 14 and positions the adhesive free side of the bandage against base portion 12 of the wrapper material. The second fold is taken along line 9 to position the adhesive coated surface of the bandage against cover portion 11 of the wrapper material which includes an adhesive release coating on the surface presented to the adhesive.

Cover portion 11 of the wrapper material is sealed by heat or other suitable means to the underlying portion of the wrapper material along line 8, leaving edge 20 free to form a pull tab for subsequent opening of the package as illustrated in FIG. 3. Lines 7 in FIG. 3 extending transversely to the longitudinal direction of the composite folded material define the lines along which the material will be cut with edge sealing to obtain individual wrapped bandages.

FIG. 4 is a view in perspective of a single packaged bandage 10 produced from the materials of FIG. 1 with cover panel 11 of the envelope peeled back to show the enclosed bandage which includes backing strip 13 having adhesive coated area 16 and centrally located wound covering pad 17.

Base panel 12 of the envelope is folded back at 14 and secured to bandage backing strip 13 through a line of perforations at 15. Cover panel 11 of the package is heat sealed to base panel 13 along the side edges at 23 and, prior to being peeled back, was further heat sealed to the folded back end portion of the base panel at seal lines 18 and 19. As explained above, seal lines 18 and 19 are set back from the end of panel 11 to provide pull tabs for use in opening the package.

Inside surface 21 of cover panel 11 is provided with an adhesive release coating to permit removal of the cover panel without dislodging the adhesive bandage from its attachment to base panel 12. Securing backing strip 12 to the end of the underlying base panel through perforated line 15 further assures that the adhesive bandage will remain secured to the base panel as the cover panel is peeled back.

FIG. 5 is a schematic representation of the packaged bandage of FIG. 5 in expanded cross section through the length of the package to further illustrate the construction of the bandage and enclosing envelope.

FIG. 6 depicts the package of FIG. 5 in cross section through line 6—6 of FIG. 5 to illustrate the composition of the sealed side edges 23 in the central pad area of the bandage, with the width of the sealed edges and other bandage dimensions exaggerated for clarity of illustration.

Figure 7:
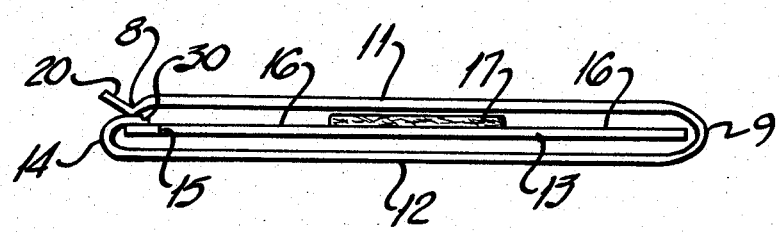
FIG. 7 is an expanded schematic side view through the center of an alternative package construction.

FIG. 7 is a schematic representation of an alternative configuration of a packaged bandage in accordance with the present invention wherein bandage backing material 13 is heat sealed to the end of base panel 12 at 30. A line of perforations at 15 allows the bandage to be readily separated from the base panel when the bandage is applied. In this embodiment of the present invention, bandage backing material 13 is secured to the wrapper material before folding to enclose the bandage within the wrapper, and may be of a composition which is different than that of the wrapper material, provided that the materials are compatible for heat sealing.

Figure 8:
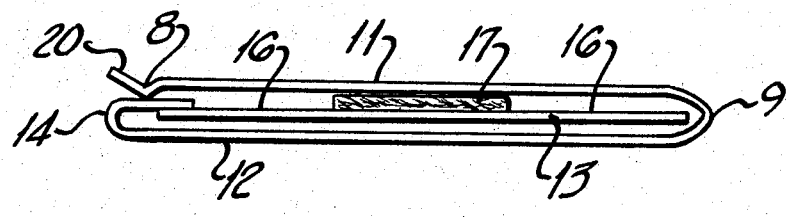
FIG. 8 is an expanded schematic side view through the center of a further package construction.

FIG. 8 is a schematic representation of a further embodiment of the present invention wherein bandage backing material 13 is contained within an end fold of base panel 12 and is secured thereto by the seal along the side edges over the area of the end fold. Optionally the edge of base panel 12 is left free of adhesive release coating so that the bandage material may be adhesively secured thereto during the manufacturing process and before sealing the side edges.

Figure 9:
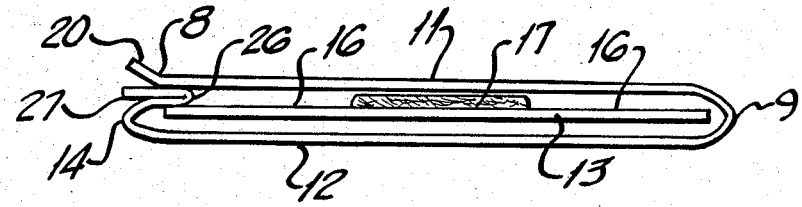
FIG. 9 is an expanded schematic side view through the center of a further alternative package construction.

FIG. 9 is a schematic representation of a variation of the bandage of FIG. 8 wherein the end of the base panel has a reverse fold at 26 to provide second pull tab 27 for easy opening of the package during application of the bandage. Pulling tab 27 to unfold the end of the base panel breaks the side edge seal and releases the bandage from the envelope.

Figure 10:
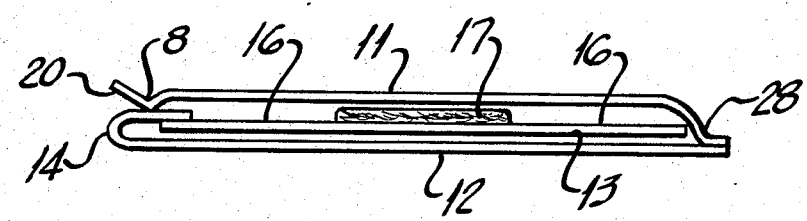
FIG. 10 is an expanded schematic side view through the center of a still further alternative package construction.

FIG. 10 is a schematic representation of a variation of the package of FIG. 8 wherein cover panel 11 and base panel 12 are separate panels joined by a seal along edge 28 distal from the pull tabs. This optional method of construction may be utilized with any of the package constructions described above.

The packaged bandages of the present invention are characterized by the backing strip of bandage portion having the same width as the panels of the envelope with the edge of the backing strip laminated between the panels of the envelope along the side edges. The packaged bandages are further characterized by having pull tab opening means at one end of the package, and having the end of the bandage backing strip detachably secured to the base panel at the end of the package proximal to the pull tab opening means. The bandage is thereby assured of remaining on the base panel as the cover panel is removed and until the bandage is applied and the base panel deliberately separated from the bandage.

The materials used to construct the bandages of the present invention may be of any composition which permits the backing strip of the bandage to be sealed to the panels of the envelope along the edges thereof as herein described by heat sealing or other suitable means. All vinyl film construction is envisioned as a preferred embodiment in the manufacture of a low cost bandage in accordance with the present invention.

The bandage backing material may be polyurethane, vinyl or other plastic film or a woven, knitted or nonwoven fabric. The adhesive may be any acrylate or other tacky pressure sensitive emulsion or melt adhesive which is non-irritating to skin and suitable for use on bandage materials. The wrapper material may be plastic film, nonwoven fabric, paper or plastic coated paper. All components are preferably heat sealable to facilitate assembly of the final package although other sealing means such as ultrasonic welding or adhesives are contemplated and within the scope of the present invention.

The bandage pad material, if utilized as a continuous length of pad, is preferably heat bondable, absorbable nonwoven fabric which provides loft and absorbency in the pad area while being compressible and heat fusible to avoid interfering with the heat sealing of the edges of the package. A preferred nonwoven fabric comprises a mixture of cellulose or other absorbent fibers and polyethylene or other heat fusible fibers which impart the necessary heat fusible characteristics to the fabric. The heat-fusible fibers are interspersed throughout the fabric and are preferably present in an amount of at least 10% by weight. The fabric preferably has sufficient thickness or bulk so that the triple-layered pad has a thickness of at least 2 mm in the final bandage. Nonwoven fabrics useful in the practice of the present invention are known in the art for use in other applications. See, for example, U.S. Pat. Nos. 2,774,128; 3,067,747; 4,083,913; 4,160,159; and 4,307,721.

The bandage pad material is preferably provided with a wound release surface which may be a polymeric film or heat glazed nonwoven fabric. These and other variations in materials and methods of construction will be readily apparent to those skilled in the art and are included within the scope of the present invention.

I claim:

1. A packaged adhesive bandage comprising an adhesive bandage and an envelope therefor,
said bandage comprising a backing strip having side edges and end edges and having a tacky adhesive coating on one surface thereof,
said envelope comprising a cover panel and opposing base panel with side edges and end edges of said panels sealed around the periphery thereof to enclose said bandage, the backing strip of said bandage being laminated between the panels of said envelope along the side edges thereof,
a portion of said cover panel and said base panel of said envelope extending beyond the seal at one end thereof to provide pull tab means for opening said envelope,
the end of said backing strip proximal to said pull tab means being detachably secured to the base panel of said envelope,
the cover panel of said envelope including an adhesive release surface overlying the adhesive coated surface of the backing strip of said bandage,
whereby when said cover panel is separated from said package, said bandage remains in position on said base panel with the adhesive coated surface exposed.

2. The package of claim 1 wherein said envelope is heat sealed around the periphery thereof.

3. The package of claim 1 wherein said bandage includes a wound covering pad secured to the central area of the adhesive coated surface thereof.

4. The package of claim 3 wherein said wound covering pad is constructed of a heat fusible material which is laminated between the panels of said envelope along the side edges thereof.

5. The package of claim 1 wherein the end of said envelope base panel proximal to the pull tab is folded back and extends into the interior of the sealed package, and the backing strip of said bandage is detachably secured to said end of said base panel.

6. The package of claim 5 wherein said backing strip of said bandage is an extension of said base panel and is detachably secured thereto through a line of perforations.

7. The package of claim 5 wherein said backing strip of said bandage underlies said folded back portion of said support panel and is heat sealed thereto along the side edges thereof.

8. The package of claim 7 wherein said backing strip of said bandage underlying said folded back portion of said support panel is additionally adhesively secured thereto.

9. The package of claim 5 wherein said backing strip of said bandage is heat sealed to said folded back portion of said support panel along the end edge thereof and includes a line of perforations adjacent said heat seal line.

10. The package of claim 5 wherein the end of said base panel includes a further reverse fold and extends out from the interior of said package to provide additional pull tab means for opening said envelope.

11. The package of claim 1 wherein said cover panel and opposing base panel of said envelope are a unitary structure joined at a fold line at one end of said envelope and sealed together at the other end and along the sides thereof.

12. The package of claim 1 wherein said cover panel and opposing base panel of said envelope are separate structures sealed together at each end and along the sides thereof.

* * * * *